United States Patent [19]

Monsan

[11] 4,405,715

[45] Sep. 20, 1983

[54] ENZYMES IMMOBILIZED ON A SOLID SUPPORT CONTAINING CELLULOSE AND LIGNIN

[75] Inventor: Pierre Monsan, Toulouse, France

[73] Assignee: Beghin-Say, S.A., Thumeries, France

[21] Appl. No.: 290,804

[22] PCT Filed: Aug. 3, 1981

[86] PCT No.: PCT/FR80/00185

§ 371 Date: Dec. 18, 1980

§ 102(e) Date: Aug. 3, 1981

[87] PCT Pub. No.: WO81/01860

PCT Pub. Date: Jul. 9, 1981

[30] Foreign Application Priority Data

Dec. 21, 1979 [FR] France ............................... 79 31382

[51] Int. Cl.$^3$ ..................... C12P 19/02; C12N 11/12; C12N 11/06

[52] U.S. Cl. .................................. 435/105; 435/179; 435/181

[58] Field of Search ............... 435/178, 179, 181, 100, 435/201, 176, 105

[56] References Cited

U.S. PATENT DOCUMENTS

| | | |
|---|---|---|
| 3,669,841 | 6/1972 | Miller ................................. 435/176 |
| 3,706,633 | 12/1972 | Katchalski et al. ................. 435/178 |
| 3,741,871 | 6/1973 | Weeks et al. ........................ 435/179 |
| 3,841,969 | 10/1974 | Emery et al. ................... 435/179 X |
| 3,947,352 | 3/1976 | Cuatrecasas et al. ............ 435/178 X |
| 3,960,666 | 6/1976 | Bourdeau et al. .................. 435/179 |
| 4,013,514 | 3/1977 | Wildi et al. .................... 435/179 X |
| 4,279,998 | 7/1981 | Shahani et al. ................. 435/178 X |

OTHER PUBLICATIONS

Zaborsky, O., Immobilized Enzymes, CRC Press, Cleveland, Ohio, 1974, (pp. 6-7).

*Primary Examiner*—David M. Naff
*Attorney, Agent, or Firm*—A. W. Breiner

[57] ABSTRACT

Enzymes are immobilized on a solid support material containing essentially cellulose and lignin by a process involving oxidation of the support to provide aldehyde groups, amination of the oxidized support by reacting a diamine with the aldehyde groups, reduction of the aminated support to produce stabilized aminated groups, activation of the aminated groups by reacting the groups with a dialdehyde and immobilization of an enzyme by covalent coupling of the enzyme to the activated groups of the support. The enzyme may be invertase and the immobilized invertase can be used to treat a sugar syrup.

17 Claims, No Drawings

ENZYMES IMMOBILIZED ON A SOLID SUPPORT CONTAINING CELLULOSE AND LIGNIN

TECHNICAL FIELD

The present invention relates to a process for fixing an enzyme on a water-insoluble solid support. It also comprises as its object an enzyme-support complex and an application procedure for such a complex.

PRIOR ART

For several years already work has been done to render insoluble enzymes or other agents such as antibodies, antigens or nuclear acids so as to obtain the capability of purifying, modifying, or insulating certain substances with which these "catalysts" form complexes or else favor a specific reaction.

The endeavors to achieve insoluble enzyme-support combinations are due to the fact that numerous reactions involve enzymes, and not only is there an economic incentive to recover an expensive enzyme, but moreover the reaction products should not be soiled.

Numerous works have been performed on the selection of the supports and the methods of fixing or combining enzymes: the scientific literature is quite abundant and describes several supports such as silica, glass, synthetic polymers, polysaccharides and in particular cellulose.

Most of the publications relating to cellulose refer to a very pure cellulose, whereas as a rule cellulose is associated with hemicelluloses and lignin.

Thus, N. WELIKY and H. H. WEETHALL in 1965 (Immunochemistry Pergamon Press, Vol. 2, pp. 293-322) published an article entitled "The Chemistry and Use of Cellulose Derivatives for the Study of Biological Systems."

The cellulose reactivity is that of a polyalcohol and can be subjected to oxidation, esterification, etherification, halogenation reactions, etc.

In particular, oxycelluloses are coupled to alcohols, amines or proteins, forming thereby esters or amides.

In view of the reactions used to modify cellulose, it is clear why as a rule the attempt has been made to eliminate lignin, a crosslinked polymer of which the numerous reactive groups use up the bodies being employed to modify the cellulose or else inhibit the desired reactions.

However, the U.S. Pat. No. 3,841,969 (A. N. EMERY et al.) describes a method for preparing immobilized enzymes by chelation with a metal complex and with substances comprising hydroxyl functions: microcrystalline cellulose, diethylaminoethylated cellulose, carboxylmethyl cellulose, but also sawdust and wood chips.

In addition to the difficulty of using industrially such metal chlorides as titanium tetrachloride or tin chloride, it is also known that the chelates are not stable over wide pH ranges.

On the other hand, the French Pat. No. 2,247,472 (SNPA) describes a method for fixing enzymes on lignin associated cellulose and indicates in surprising manner that the cellulose-enzyme association reaction is enhanced by lignin present by 5 to 25% by weight and preferably 10 to 20% by weight.

Cereal stalk granules between 0.3 and 10 mm in size first are surface-delignified and following washing are treated with thionyl chloride in pyridine, and lastly are placed in contact with a buffered enzyme solution.

It appears obvious that the lignin exerts no favorable influence at all on the reaction that allows immobilizing the enzyme, because it is mandatory to begin with a stage of surface delignification of the granules.

DESCRIPTION OF THE INVENTION

The present invention concerns a method for obtaining enzyme derivatives wherein the enzyme is fixed by a covalent bond on a water-insoluble support, characterized by the following steps:

(a) a substrate essentially containing cellulose and lignin is washed with water, (b) controlled oxidation of the oside fraction of the substrate, (c) condensation of a diamine on the aldehyde groups of the oxidized support, (d) stabilization by reduction of the amine-substrate bond, (e) activation by means of a dialdehyde of the aminated groups, (f) coupling the enzyme on the activated substrate.

Preferably the oxidizer in stage (b) is sodium periodate, the diamine is ethylene diamine, the reducer is sodium borohydride or cyanoborohydride, dialdehyde, glutaraldehyde. The enzyme in particular may be invertase, saccharase levan, lactase or dextran sucrase.

Even though the whole of the support containing cellulose and lignin can be used, especially significant results are obtained using the most lignified fraction of cereal stalks, in particular maize (i.e., "corn") stalks.

The maize stalks consist of:

(1) soft elements called "feeds" containing for the most part cellulose and proteins, meant for cattle feed, (2) hard elements called "grits" containing a high proportion of lignin (exceeding 25%), cellulose and xylanes.

As a rule, these elements are ground and due to their hardness are used as fillers or abrasives. The quasi-spherical particles that are obtained vary in sizes between a few dozen microns and several millimeters.

Another object of the invention is an enzyme derivative wherein the enzyme is covalently bonded to the support and characterized in that the support consists of that part of the cereal stalks of which the lignin content exceeds 25%, the enzyme being invertase, saccharase levan, lactase or dextran sucrase.

Another object of the invention concerns a treatment process of juices sweetened by means of enzymes fixated on that part of the cornstalks of which the lignin content exceeds 25%.

In particular, concentrated saccharose juice is being treated by being made to pass through a bed of cornstalk particles acting as the invertase support for the purpose of obtaining an invert syrup.

In another implementation of the invention, saccharose juice is being treated by being made to pass over a bed of cornstalk particles acting as the support for the saccharase levan: a juice containing polyfructose and glucose is obtained.

The examples provided below better explain the invention:

Invertase is an enzyme catalyzing the hydrolysis of saccharose into glucose and fructose, and for which the invention provides the fixation on solid water-insoluble substrates containing both cellulose and lignin.

More particularly, the fixation of the "hard" part of the cornstalk with a lignin content in excess of 25% has been researched. This "hard" part was ground in a manner to obtain particles with diameters between 170 and 280 microns. Their apparent density is 0.4 kg/liter in the dry state and 1.8 kg/liter in the wet state. Their specific surface is 1 m²/g.

The activity of the enzyme preparation is ascertained by establishing contact for 4 minutes at 40° C. between 10 ml of 0.4 M saccharose solution in 0.1 M acetate buffer, and 0.1 ml of invertase solution (or immobilized invertase solution) in the same buffer.

The reaction is stopped by adding 5 ml of the medium to 0.5 ml of 2 N soda solution. Then the content in released reducing sugars is determined by the dinitrosalicylate method (mn absorbance reading). Calibration is obtained using equimolecular solutions of glucose and fructose in the 0.1 M acetate buffer (pH=4.5).

One enzyme activity unit (U) is defined as that amount of enzyme causing the release of 1 g of reducing sugars a minute under the test conditions.

The specific activity of the invertase preparation (SIGMA Chem. Co.) is 93.3 U per mg of enzyme.

The treatment procedure of the cornstalk particles comprises the following stages:

(a) preliminary distilled-water washing for 24 h at 25° C. to eliminate the soluble substances, followed by drying at 60° C., (b) controlled oxidation by placing a sample of 100 mg in contact with 20 ml of sodium metoperiodate solution in distilled water at 25° C., in darkness, (c) amination by reacting oxidized stalks with 20 ml of diamine in methanol solution at 25° C.

Concerning this stage, the following diamines were tested:
ethylenediamine
hexamethylenediamine
octamethylenediamine
diamino dicyclohexyl methane
diamino diphenyl methane, (d) reduction at 25° C. by placing in contact either 25 ml of sodium borohydride solution in 0.05 M carbonate buffer and at a pH of 10.5 or in methanol, or 20 ml of sodium cyanoborohydride solution in 0.05 M phosphate buffer at a pH of 6.5, (e) activation by a glutaraldehyde solution in a 0.05 M pyrophosphate buffer at a pH of 8.6 and at 25° C., (f) fixation of the invertase in solution in 0.1 M acetate buffer at a pH of 4.5 and at 4° C.

Each stage is followed by two washings of the stalks by return to suspension for 15 min in 20 ml of the medium used during the previous stage—containing no reactive sample—and then by three washings by return to suspension during the following stage.

The various stages can be schematically shown in principle as follows:

Oxidation

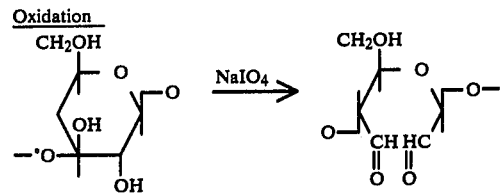

Amination

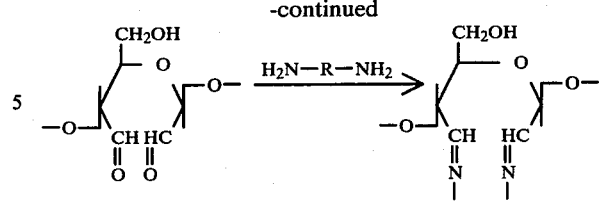

Reduction

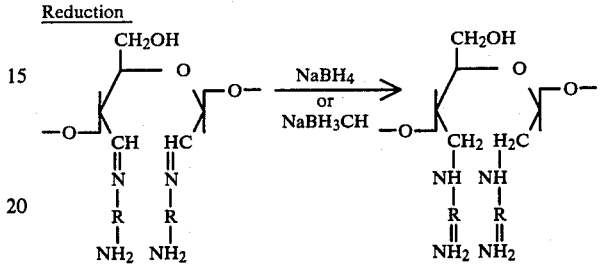

Activation

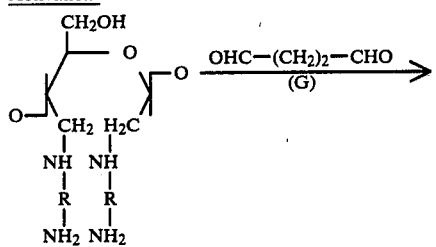

Immobilization

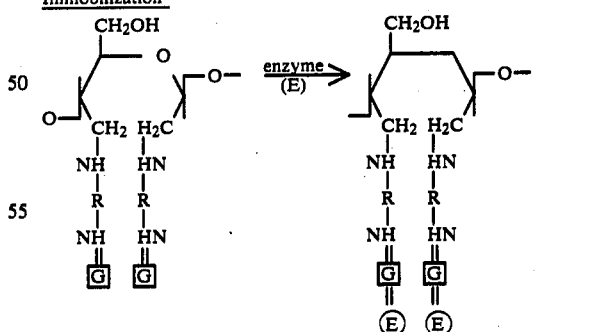

Following grafting of the enzyme, the support is washed with 20 ml of 1 M NaCl solution in distilled water in order to eliminate the simply adsorbed invertase. Then the activity retained on the sample of the stalks is ascertained.

Obviously the attempt was made to optimize the various stages:

(1) Oxidation

(a) Effect Of The Sodium Periodate Concentration

The experimental conditions selected were as follows:

TABLE I

| Stage | Oxidation | Amination | Reduction | Activation | Fixation |
|---|---|---|---|---|---|
| Product | $NaIO_4$ | $C_2H_8N_2$ | $NaBH_2$ | glutaraldehyde | invertase |
| Medium | $H_2O$ | $CH_3OH$ | $CH_3OH$ | pyrophosphate buffer | acetate buffer |
| pH | — | — | — | 8.6 | 4.5 |
| Concentration | variable | 3M | 10 g/l | 1.25% | 0.5 g/l |
| Time (h) | 30 | 72 | 4 | 5 | 10 |

By varying the $NaIO_4$ concentration, the results in Table II were obtained:

TABLE II

| Concentration | | | | |
|---|---|---|---|---|
| $NaIO_4$ (M) | 0 | 0.05 | 0.2 | 0.4 |
| Activity (U/g of stalks) | 0 | 0.28 | 1.28 | 1.33 |

By carrying out the reduction with sodium cyanoborohydride (10 g/l concentration, phosphate buffer pH 6.5, time=2 h) in lieu of sodium borohydride, all other conditions being the same, the results listed in Table III are obtained:

TABLE III

| Concentration | | | | |
|---|---|---|---|---|
| $NaIO_4$ (M) | 0 | 0.05 | 0.2 | 0.4 |
| Activity (U/g of stalks) | 0 | 0.53 | 2.20 | 2.18 |

Accordingly, whatever the reducing method used, the optimal enzyme grafting is obtained for a sodium metaperiodate concentration in excess of 0.2 M.

(b) Effect Of Duration

The metaperiodate concentration being set at 0.2 M and all other test conditions being identical with those selected in (a) (except that the methanol reducing medium is replaced by a phosphate buffer), the results listed in Table IV are obtained:

TABLE IV

| Time of Oxidation (h) | 0 | 2 | 5 | 8.75 | 13 | 24 | 48 |
|---|---|---|---|---|---|---|---|
| Activity (U/g of stalks) | 0 | 0.42 | 0.55 | 0.77 | 0.97 | 1.49 | 1.53 |

The optimal oxidation time is set at 30 h. Be it noted that the oxidation appears to proceed by two phases a first rapid phase (0–2 h) a second slower phase (2–24 h).

(2) Oxidation

(a) Effect Of The Nature Of The Diamine

The oxidation time by 0.2 M sodium periodate being set at 30 h, the other test conditions being those selected in 1(a), the results listed in Table V are obtained:

TABLE V

| Diamine | $C_2H_8N_2$ | $C_6H_{16}N_2$ | $C_8H_{20}N_2$ | $C_{13}H_{26}N_2$ |
|---|---|---|---|---|
| Activity (U/g of stalks) | 1.28 | 0.61 | 0.43 | 0.40 |

Accordingly the highest enzyme activities are obtained when using ethylenediamine ($C_2H_8N_2$).

(b) Effect Of The Ethylenediamine Concentration

The test conditions being those of example 1(a) (except that the time of oxidation is set at 13 h and that the methanol reducing medium is replaced by a carbonate buffer), the results listed in Table VI are obtained:

TABLE VI

| Diamine Concentration (M) | 0 | 0.05 | 0.5 | 1 | 5 | 7.5 |
|---|---|---|---|---|---|---|
| Activity (U/g of stalks) | 0 | 0.50 | 0.72 | 0.97 | 1.24 | 1.23 |

It will be noted that a substantial catalytic activity is obtained for a relatively low diamine concentration (0.05 M). However, the optimal concentration is taken to be 3 M.

(c) Effect Of Duration

The test conditions are the following:

TABLE VII

| Stage | Oxidation | Amination | Reduction | Activation | Fixation |
|---|---|---|---|---|---|
| Product | $NaIO_4$ | $C_2H_8N_2$ | $NaBH_3CN$ | glutaraldehyde | invertase |
| Medium | $H_2O$ | $CH_3OH$ | phosphate buffer | pyrophosphate buffer | acetate buffer |
| pH | — | — | 6.5 | 8.6 | 4.5 |
| Concentration | 0.2 M | 3M | 10 g/l | 1.25% | 0.5 g/l |
| Duration (h) | 30 | variable | 2 | 5 | 10 |

The results are listed in Table VIII:

TABLE VIII

| Amination Time (h) | 0 | 17 | 24 | 48 | 72 | 79 |
|---|---|---|---|---|---|---|
| Activity (U/g of stalks) | 0 | 0.98 | 1.21 | 1.84 | 2.20 | 2.12 |

Accordingly a time of 72 h was set for the amination stage.

(3) Reduction

(a) Effects Due To The Kind And Concentration Of The Reducer

The test conditions are as follows:

TABLE IX

| Stage | Oxidation | Amination | Reduction | Activation | Fixation |
|---|---|---|---|---|---|
| Product | NaIO$_4$ | C$_2$H$_8$N$_2$ | variable | glutaraldehyde | invertase |
| Medium | H$_2$O | CH$_3$OH | variable | pyrophosphate buffer | acetate buffer |
| pH | — | — | — | 8.6 | 4.5 |
| Concentration | 0.2 M | 3M | variable | 1.25% | 0.5 g/l |
| Duration (h) | 30 | 72 | 2 | 5 | 10 |

The results are listed in Table X:

TABLE X

| | Reducer Concentration (g/l) | | |
|---|---|---|---|
| Reducer | 0 | 10 | 20 |
| NaBH$_4$ (0.05 M carbonate buffer) pH 10.5 | 1.11 | 1.29 | 1.28 |
| NaBH$_3$CN (0.05 M phosphate buffer) pH 6.5 | 1.11 | 2.20 | 2.25 |

Accordingly cyanoborohydride is the more effective reducer.

(b) Effect Of The Time Of Reaction

The test conditions are the following:

TABLE XI

| Stage | Oxidation | Amination | Reduction | Activation | Fixation |
|---|---|---|---|---|---|
| Product | NaIO$_4$ | C$_2$H$_8$N$_2$ | NaBH$_3$CN | glutaraldehyde | invertase |
| Medium | H$_2$O | CH$_3$OH | phosphate buffer | pyrophosphate buffer | acetate buffer |
| pH | — | — | 6.5 | 8.6 | 4.5 |
| Concentration | 0.2 M | 3M | 10 g/l | 1.25% | 0.5 g/l |
| Duration (h) | 30 | 72 | variable | 5 | 10 |

The test results are listed in Table XII:

TABLE XII

| Reducing Time (h) | 0 | 2 | 4 |
|---|---|---|---|
| Activity (U/g of stalks) | 1.11 | 2.10 | 2.15 |

(4) Activation (a) Effect Of The Concentration Of Glutaraldehyde And Of Duration The test conditions are the same as for test 3(b).
The results, expressed in U/g of stalks are provided in Table XIII:

TABLE XIII

| | Glutaraldehyde Concentration (%, v/v) | | | | |
|---|---|---|---|---|---|
| Activation Time (h) | 0 | 0.5 | 1.25 | 5 | 10 |
| 0 | — | — | 1.34 | — | — |
| 0.5 | — | — | 1.42 | — | — |
| 3 | — | — | 1.70 | — | — |
| 5 | 1.34 | 2.26 | 2.33 | 2.30 | 2.32 |
| 11 | — | — | 2.34 | — | — |

Accordingly, the optimal concentration is 1.25% and the duration is 5 h.

(5) Invertase Fixation (a) Effect Of The Invertase Concentration And Of The Fixation Time The test conditions are the same as for test 3(b).
Table XIV lists the results.

TABLE XIV

| | Invertase Concentration (g/l) | | | | | |
|---|---|---|---|---|---|---|
| Fixation Time (h) | 0.05 | 0.1 | 0.5 | 1 | 2 | 5 |
| 10 | 0.39 | 1.01 | 2.36 | 3.30 | 3.52 | 3.56 |
| 24 | — | — | — | 3.82 | — | — |
| 35 | — | — | — | 4.08 | — | — |

Accordingly, the optimal invertase concentration is 2 g/l and the optimal duration for fixation is 30 h.

Table XV summarizes the optimal conditions for fixating invertase on cornstalks:

TABLE XV

| Stage | Oxidation | Amination | Reduction | Activation | Fixation |
|---|---|---|---|---|---|
| Product | NaIO$_4$ | C$_2$H$_8$N$_2$ | NaBH$_3$CN | glutaraldehyde | invertase |
| Medium | H$_2$O | CH$_3$OH | phosphate buffer | pyrophosphate buffer | acetate buffer |
| pH | — | — | 6.5 | 8.6 | 4.5 |
| Concentration | 0.2 M | 3M | 10 g/l | 1.25% | 2 g/l |
| Duration (h) | 30 | 72 | 2 | 5 | 30 |

Other immobilization methods for invertase on cornstalks were tested:
absorption
absorption followed by crosslinking due to glutaraldehyde
direct fixation on oxidized stalks
grafting aromatic diamines activated by diazotation
oxidizing aldehydes into acids, followed by activation by the nitridation process.

None of these methods offered results comparable to those obtained by the procedure of the invention.

In particular, the method described in the French Pat. No. 2,247,472 was carried out; two supports were used:
(1) a sample of whole stalks mechanically ground and sifted so as to only keep the fraction with a diameter between 100 and 200 microns,
(2) a sample of "grits" with a diameter between 170 and 280 microns.

The invertase was immobilized by placing in contact 100 g of activated supports with 20 ml of an invertase solution (SIGMA Chem. Co. I 5875) at 2 g/l in 0.1 M acetate buffer at a pH of 4.5, for 30 hours with rotary agitation and at 4° C.

Following exhaustive elimination of the unfixed enzyme by washing the supports with 0.1 M acetate buffer at a pH of 4.5, the retained activation was determined by measuring the amount of reducing sugars (glucose and fructose) which were released by the action of the enzyme on a 0.4 M saccharose solution at 40° C.

Table XVI lists the results.

TABLE XVI

| Immobilization Method | Support | Enzyme Activity |
| --- | --- | --- |
| French Patent No. 2,247,472 | whole stalks | 0.049 |
|  |  | 0.0505 |
|  | grits | 0.036 |
|  |  | 0.015 |
| Present Invention | whole stalks | 2.12 |
|  |  | 2.10 |
|  | grits | 3.10 |
|  |  | 2.94 |

The enzyme activities obtained with supports treated by the invention are 40 to 80 times higher than those obtained with the same supports treated according to the French Pat. No. 2,247,472.

Again the possibilities of continuously using invertase immobilized on cornstalks in a reactor with a 10 ml fixed volume, supplied with 1.9 g of stalks bearing the enzyme were tested. This reactor was placed in a thermostatically controlled enclosure and kept at 40° C. and was fed continuously by means of variable concentrations of saccharose solutions in 0.1 M acetate buffer at a pH of 4.5.

Table XVII lists the results:

TABLE XVII

| Initial Saccharose Concentration | Feed Rate (l/h) | | | | | | |
| --- | --- | --- | --- | --- | --- | --- | --- |
|  | 0.15 | 0.40 | 0.68 | 0.82 | 0.97 | 1.05 | 1.2 |
| 0.1 M (34.2 g/l) | 100% | 100% | 100% | 100% | 100% | 100% | 100% |
| 1 M (342 g/l) | 97% | 96% | 80% | 73% | 62% | 57% | 53% |

Accordingly, maximal hourly productivities are obtained, which are:
22 g of saccharose hydrolyzed per hour and per g of stalks for an initial concentration of 0.1 M
117 g of saccharose hydrolyzed per hour and per g of stalks for an initial concentration of 1 M saccharose.

The following experiments were run in order to establish the industrial application of the continuous hydrolysis of saccharose juice:

Two reactors are used:
Reactor A: total volume is 100 ml, stalk quantity is 44.1 g;
Reactor B: total volume is 1 liter, stalk quantity is about 400 g.

A commercial invertase preparation (SIGMA Chem. Co.) was immobilized on cornstalks with an average diameter of 0.81 mm. The results obtained from the two successively prepared reactors are listed in Table XVIII:

TABLE XVIII

|  | Activity (U)[a] | % Immobilization Efficiency[b] |
| --- | --- | --- |
| Reactor A | 0.32 | 3 |
| Reactor B | 0.84 | 16 |
| Optimal Conditions[c] | 1.10 | 19 |

[a]The activity is expressed in g of reducing sugars released per mm and per g of support for the test conditions.
[b]The immobilization efficiency is expressed as the ratio of the activity per mg of immobilized enzyme to the activity per mg of free enzyme.
[c]The optimal immobilization conditions were previously determined for samples of 100 mg of stalks.

It will be noted that the problem of extrapolating the immobilization of the invertase for a scale of supports 100 mg to the scale of stalks up to 1 kg was resolved because the results for Reactor B are close to those obtained under optimal conditions.

Table XIX lists the results concerning the production of glucose and fructose (expressed as g of reducing sugars produced per h and per g of stalks).

The maximum productivity was determined, respectively, for an initial saccharose conversion rate of 90% to 100%.

TABLE XIX

| Reactor Volume | Saccharose Concentration | Temperature | Maximum Productivity (g/h × g of support) | |
| --- | --- | --- | --- | --- |
|  |  |  | For 90% Conversion | For 100% Conversion |
| 0.1 liter | 1 M, (342 g/l) | 40° | 3.55 | 2.32 |
|  | 2 M | 40° | 2.90 | 2.10 |
|  | (684 g/l) | 50° | 4.10 | 2.40 |
|  |  | 55° | 5.30 | 3.30 |
|  |  | 60° | 5.00 | 2.50 |
| 1 liter | 1 M | 40° | 9.65 | 5.25 |
|  | 2 M | 40° | 6.50 | 4.90 |
|  |  | 50° | 11.00 | 6.50 |
|  |  | 55° | 7.90 | 6.50 |
| Solution 70 BRIX (Akg/l) |  | 50° | 5.40 | 1.90 |

The extrapolation from the 100 ml reactor results to those of the 1 liter reactor is essentially linear, the maximum productivities being in the same ratio as the enzyme activities per g of support (0.32 U and 0.84 U, respectively).

The immobilized invertase hence reveals itself being exceedingly effective as for the results obtained from the 1 liter reactor for a solution of 68.4% saccharose, a productivity (at 50° C.) of 11 g of reducing sugars a day is obtained for the 1 liter volume reactor (the conversion rate being 90%).

The catalyst stability is very good as no significant drop in activity at all was noted after 20 days of continuous operation (at 40° C., 50° C., 55° C., and 60° C.) for the 1 liter reactor.

A positive treatment was obtained for a remolten pure sugar syrup or an industrial syrup from beets or sugar cane at a temperature between 40° and 60° C. and about 70 Brix.

However, the maximum productivity is about twice less than for an approximately 70% saccharose solution.

Nevertheless, solutions equally highly concentrated in saccharose may be continuously hydrolyzed in principle, provided the syrup be preheated to lessen its viscosity.

It must be stressed that the enzyme derivatives obtained in conformity with the invention allow the continuous treatment of very high saccharose concentration juices without thereby decreasing their activities.

The appreciable advantage thus obtained industrially is easily seen; there is less bulk of equipment, saving in energy, and long life of the enzyme support.

I claim:

1. In a process for preparing enzyme derivatives wherein the enzyme is fixed by a covalent bond onto a water-insoluble support by the steps of
   (a) washing a support material having an oside fraction and containing essentially cellulose and more than 25% lignin with water;
   (b) oxidizing the oside fraction of the support by controlled oxidation to provide aldehyde groups;
   (c) condensing a diamine onto the aldehyde groups contained on the support provided by step (b) to provide an amine-supported bond; and
   (d) stabilizing the amine-support bond by reduction to provide stabilized aminated groups, the improvement wherein
   (i) activating the aminated groups with a dialdehyde to provide an activated support, and
   (ii) coupling the enzyme onto the activated support with a covalent bond.

2. In the process of claim 1 the further improvement wherein the dialdehyde is glutaraldehyde.

3. In the process of claim 1 the further improvement wherein the enzyme is invertase.

4. In the process of claim 1 the further improvement wherein the said activation of the aminated groups is carried out using glutaraldehyde at a 1.25% concentration in 0.05 M pyrophosphate buffer medium for 5 hours, at 25° C., and the activated support is placed in contact with 2 g/l invertase solution in a 0.1 M acetate buffer for 30 hours at 4° C. to couple the enzyme to the support.

5. In the process of claim 1 the further improvement wherein the enzyme is saccharase levan, lactase, or saccharose dextran sucrase.

6. In the process of claim 1 the further improvement wherein the support is the part of cornstalks wherein the lignin content exceeds 25%.

7. In the process of claim 6 the further improvement wherein the cornstalks are in the form of quasispherical particles with diameters between 170 and 280 microns, the apparent density in the dry state being 0.4 kg/l and 1.3 kg/l in the wet state and which have a specific surface of 1 $m^2/g$ and comprise pores with a diameter of about 3,000 Å.

8. Enzyme derivative wherein the enzyme is coupled to a water-insoluble support by the process of claim 1.

9. Enzyme derivative wherein the enzyme is coupled to a water-insoluble support by the process of claim 6.

10. Enzyme derivative wherein the enzyme is coupled to a water-insoluble support by the process of claim 7.

11. Enzyme derivative wherein the enzyme is coupled to a water-insoluble support by the process of claim 3.

12. A treatment process for sweetened juice wherein the juice is made to pass in contact with an enzyme derivative prepared by the process of claim 1.

13. A treatment process for sweetened juice wherein the juice is made to pass in contact with an enzyme derivative prepared by the process of claim 6.

14. The process of claim 13 wherein the sweetened juice essentially contains saccharose.

15. The process of claim 14 wherein the enzyme is invertase.

16. The process of claim 15 wherein the sweetened juice is about 70 Brix.

17. The process of claim 16 wherein the temperature of the sweetened juice is kept between 40° and 60° C.

* * * * *